United States Patent [19]

Buchbinder et al.

[11] Patent Number: 4,815,478
[45] Date of Patent: Mar. 28, 1989

[54] STEERABLE GUIDEWIRE WITH DEFLECTABLE TIP

[75] Inventors: Maurice Buchbinder; Ronald J. Solar; Leo Roucher, all of San Diego, Calif.

[73] Assignee: Medtronic Versaflex, Inc., San Diego, Calif.

[21] Appl. No.: 175,101

[22] Filed: Mar. 31, 1988

Related U.S. Application Data

[62] Division of Ser. No. 15,249, Feb. 17, 1987, Pat. No. 4,757,827.

[51] Int. Cl.⁴ .............................................. A61B 5/00
[52] U.S. Cl. ................... 128/772; 128/657; 604/170; 604/95
[58] Field of Search .............. 128/772, 656–658; 604/95, 103, 170, 280

[56] References Cited

U.S. PATENT DOCUMENTS

| | | |
|---|---|---|
| 3,452,740 | 7/1969 | Muller . |
| 3,452,742 | 7/1969 | Muller . |
| 3,503,385 | 3/1970 | Stevens . |
| 3,521,620 | 7/1970 | Cook . |
| 3,528,406 | 9/1970 | Jeckel et al. . |
| 3,547,103 | 12/1970 | Cook . |
| 3,625,200 | 12/1971 | Muller . |
| 3,789,841 | 2/1974 | Antoshkiw . |
| 3,841,308 | 10/1974 | Tate . |
| 3,906,938 | 9/1975 | Fleischhacker . |
| 3,973,556 | 8/1976 | Fleischhacker et al. . |
| 4,003,369 | 1/1977 | Heilman et al. . |
| 4,020,829 | 5/1977 | Willson et al. . |
| 4,215,703 | 8/1980 | Willson . |
| 4,456,017 | 6/1984 | Miles . |
| 4,538,622 | 9/1985 | Samson et al. . |
| 4,545,390 | 10/1985 | Leary . |
| 4,554,929 | 11/1985 | Samson et al. . |
| 4,619,274 | 10/1986 | Morrison . |
| 4,641,654 | 2/1987 | Sampson et al. ............... 128/657 X |

Primary Examiner—Stephen C. Pellegrino
Attorney, Agent, or Firm—Kane, Dalsimer, Sullivan, Kurucz, Levy, Eisele & Richard

[57] ABSTRACT

The present invention is directed to a steerable guidewire. More specifically, the invention is directed to a guidewire which comprises flexible tubing having proximal and distal ends and inner and outer surfaces, a helically wound flexible spring coil having proximal and distal ends, the proximal end of the spring coil being attached to the flexible tubing and the distal end of the spring coil comprising stretched coils, a deflection wire extending through the flexible tubing and spring coil, the deflection wire having proximal and distal ends, optionally a control wire having proximal and distal ends, the proximal end of the control wire being attached to the spring coil proximal to the stretched coils, and a rounded tip engaging the distal end of the spring coil, the distal end of the deflection wire, and the distal end of the control wire.

20 Claims, 3 Drawing Sheets

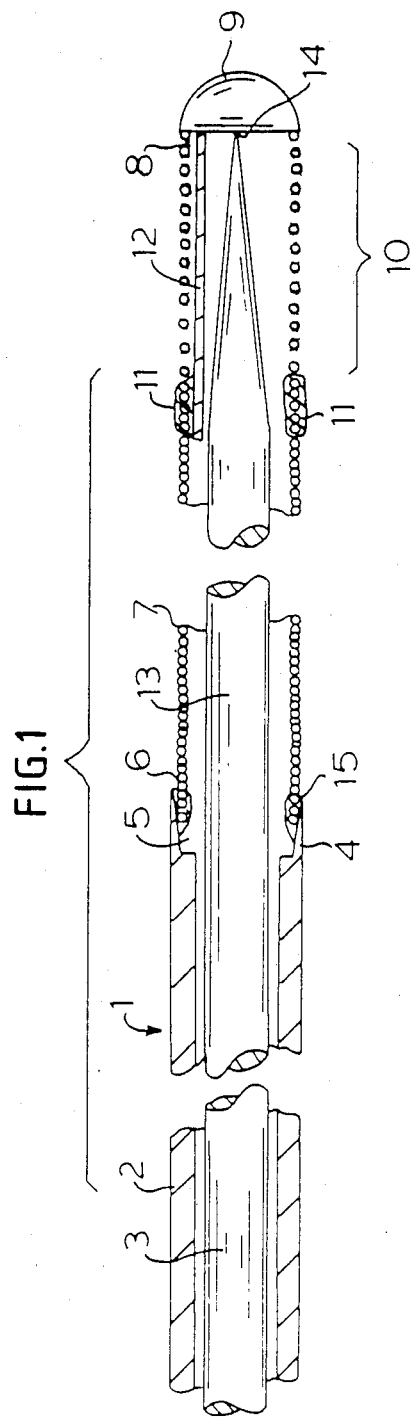
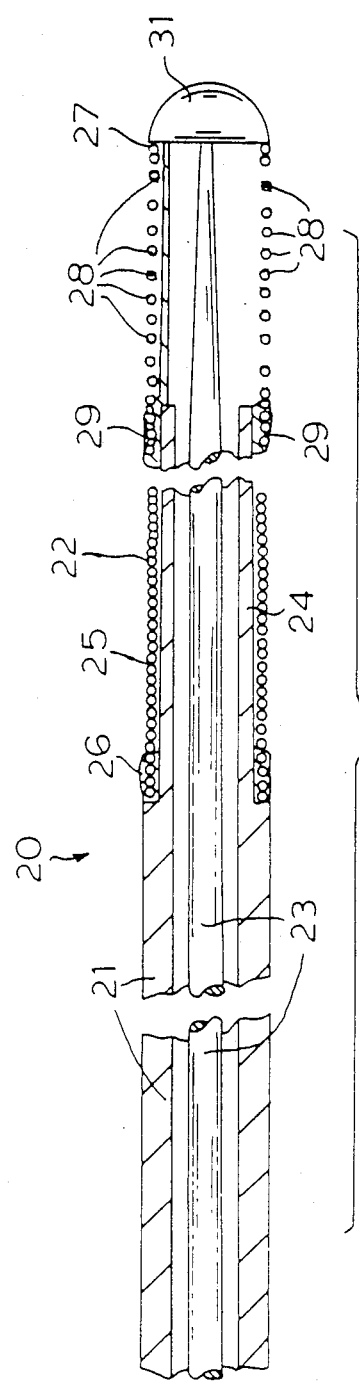

STEERABLE GUIDEWIRE WITH DEFLECTABLE TIP

CROSS-REFERENCE TO RELATED PATENT APPLICATION

This patent application is a divisional of co-pending U.S. patent application Ser. No. 015,249, filed Feb. 17, 1987 now U.S. Pat. No. 4,757,827.

FIELD OF THE INVENTION

The present invention is directed to a steerable guidewire. More particularly, the invention is directed to a steerable guidewire having enhanced steerability due to rotational control combined with a deflectable tip, which guidewire is suitable for use in connection with the insertion of a catheter into a vessel of the body.

BACKGROUND OF THE INVENTION

Coil spring guides or guidewires have been widely used for facilitating the insertion of a catheter into a vessel in the body. In some applications, a coil spring guide with a rounded tip is inserted into a vessel, a catheter is slipped about the coil spring guide until the catheter is in place, and then the guide is retracted from the vessel. In another application, a coil spring guide is first inserted into a catheter with the rounded tip of the guide extending beyond the distal end of the catheter. Then, this assembly is inserted into a vessel with the rounded tip of the coil spring guide facilitating placement of the guide and catheter tubing in the vessel without puncturing of the vessel. Once in place, the coil spring guide may be retracted, leaving the catheter in the vessel.

It is desirable in using such guidewires to provide some steering means, such as means for deflecting the tip of the guide to facilitate movement of the guidewire around or through a curved path in the vessel. There have been a number of patents directed to different constructions intended to provide a deflectable or flexible tip in a coil spring guide or guidewire. For example, such constructions are set forth in Muller, U.S. Pat. Nos. 3,452,740 and 3,452,742 Stevens, 3,503,385, Cook, 3,521,620, Jeckel et al., 3,528,406, Cook, 3,547,103, Muller, 3,625,200, Antoshkiw, 3,789,841, Tate, 3,841,308, Fleischhacker, 3,906,938, Fleischhacker et al., 3,973,556, Heilman, 4,003,369, Willson, 4,020,829, Willson et al., 4,215,703, Miles, 4,456,017, Samson et al., 4,538,622, Leary, 4,545,390, Samson et al., 4,554,929, and Morrison, 4,619,274, all of which are incorporated herein by reference.

While each of the above-mentioned patents provides guidewires having some steerability or flexibility, there is a need to develop a guidewire having better steerability. More particularly, there has been a need to develop a small diameter guidewire wherein its distal tip can be rotated and deflected to impart enhanced steerability suitable for cardiovascular applications.

OBJECTS OF THE INVENTION

It is an object of this invention to provide a steerable guidewire.

It is also an object of this invention to provide a guidewire having a deflectable tip suitable for insertion of a catheter into a vessel of the body.

It is a further object of the invention to provide a steerable guidewire comprising:

flexible tubing having proximal and distal ends and inner and outer surfaces, a helically wound flexible spring coil having proximal and distal ends, the proximal end of said spring coil being attached to the flexible tubing and the distal end of said spring coil comprising stretched coils, a deflection wire extending through the flexible tubing and spring coil, said deflection wire having proximal and distal ends, and a rounded tip attached to the distal end of the spring coil and the distal end of the deflection wire.

These and other objects of the invention will become more apparent in the discussion below.

BREIF DESCRIPTION OF THE DRAWINGS

FIG. 1 represents a substantially cross-sectional view of the distal portion of an embodiment of the invention;

FIG. 2 represents a substantially cross-sectional view of the distal portion of another embodiment of the invention;

Figure 3:
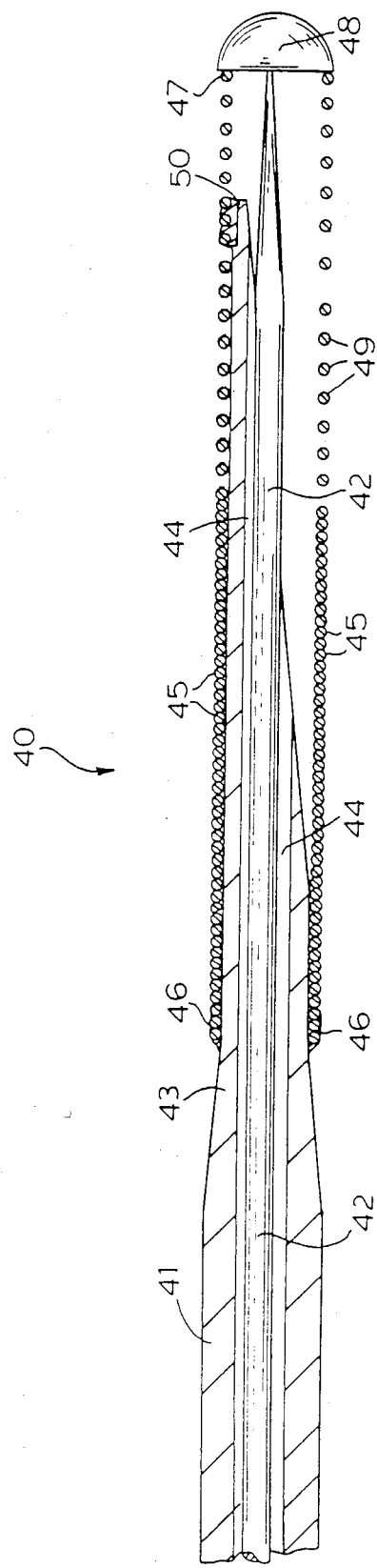
FIG. 3 represents a substantially cross-sectional view of the distal portion of a further embodiment of the invention.
Figure 4:
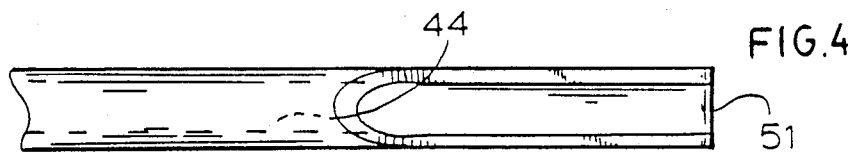
Figure 5:
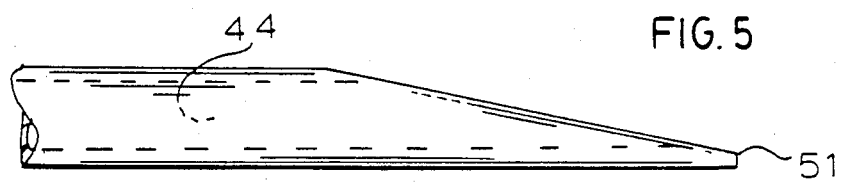

FIGS. 4 and 5 each represent a detail of the tubing shown in FIG. 3; and

Figure 6:
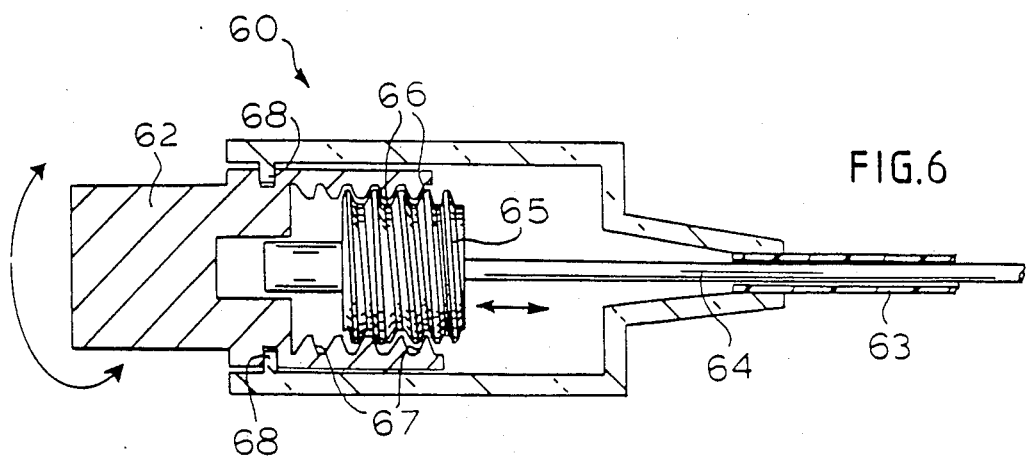

FIG. 6 represents a cross-sectional view of the proximal portion of an embodiment of the invention.

DETAILED DESCRIPTION OF THE INVENTION

The invention herein comprises a guidewire having improved steerability. Steering is provided by a steering or control wire, i.e., a deflection wire, in conjunction with tubing having a spring coil distal portion. The proximal end of the tubing is attached to a control means in which the deflection wire is engaged in a deflection knob assembly. Rotation of the deflection knob causes movement of the deflection wire in an axial direction, which causes the distal end of the guidewire to move toward or away from its longitudinal axis. Also, rotation of the control means or a member of the control means attached to the tubing and deflection wire results in torque being applied to the entire guidewire assembly, and the torque is transmitted to the distal end of the guidewire to cause desired rotation of the guidewire tip. The combination of deflection and rotation according to the invention results in enhanced steerability.

More specifically, Applicants' invention is directed to a guidewire comprised of flexible tubing having proximal and distal ends and inner and outer surfaces, a helically wound flexibile spring coil having proximal and distal ends, said spring coil being attached to the distal end of the flexible tubing, optionally at the proximal end of said spring coil, and the distal end of said spring coil comprising coils having a looser wound, i.e., stretched coils. A deflection wire extends through the flexible tubing and spring coil, said deflection wire having proximal and distal ends, and an optional control or safety wire has proximal and distal ends, the proximal end of the control wire being attached to said spring coil proximal to the stretched coils. A rounded tip engages the distal end of the spring coil, the distal end of the deflection wire, and the distal end of the control wire.

The stretched coils of the spring coil, that is, where the tension of the winding of the spring coil body is reduced to form "looser wound" coils, are extremely functional in that they facilitate deflection of the guidewire tip. Also, the distal portion of the deflection wire may be untapered or, advantageously, tapered, the tapering functioning to facilitate deflection. Preferably such a tapered distal portion is flat.

Applicants' guidewire comprises tubing, preferably flexible metal tubing such as is used in a hypodermic needle, and a spring coil. The distal end of the tubing must be suitably attached to the spring coil in such a manner to form a continuous lumen for the deflection wire. In one embodiment of the invention, the distal portion of the tubing is concentrically tapered and then angularly tapered to a point, the point being attached to the spring coil. The distal end of the spring coil has a rounded tip, and the proximal end of the guidewire is attached to a control means.

The invention can perhaps be better understood by making reference to the drawings. In the embodiment of the invention shown in FIG. 1, a guidewire 1 comprises tubing 2 having deflection wire 3 arranged axially therein. The distal end 4 of tubing 2 is recessed to provide a receptacle 5 for the proximal end 6 of spring coil 7. The distal end 8 of spring coil 7 comprises a cap or tip 9, which is rounded, preferably semi-spherical, in shape. Tip 9 is formed by a weld, a braze, solder, or an adhesive such as U.V. curing or cyanoacrylate adhesive.

The coils of spring coil 7 proximal to distal end 8 are stretched as compared to the coils in the remainder of spring coil 7. The stretched coils 10 extend from distal end 8 to adhesion point 11. A control wire 12 extends from adhesion point 11 to tip 9. Preferably stretched coils 10 are comprised of a radiopaque material such as platinum alloy or the like.

Proximal end 6 of spring coil 7 is affixed, preferably welded, brazed, or soldered, to receptacle 5 at adhesion point 15. Similarly, adhesion point 11 comprises a weld, braze, or solder point encompassing the proximal end of control wire 12.

Deflection wire 3 is tapered in its distal portion 13, preferably to a point, or substantially a point, at its distal end 14. The tapering, which begins at about the distal end 4 of the tubing 2, can be linear, stepped, or otherwise non-linear.

According to the embodiment of the invention set forth in FIG. 2, guidewire 20 comprises tubing 21 and spring coil 22. Deflection wire 23, which is located within tubing 21 and spring coil 22, extends the length of guidewire 20. The distal portion 24 of tubing 21 is recessed such that the proximal portion 25 of spring coil 22 fits thereover. The proximal portion 25 of spring coil 22 is affixed to tubing 21, preferably by welding, brazing, or soldering, at adhesion point 26.

Deflection wire 23 is tapered at its distal end. Preferably said tapered portion is substantially flat.

The coils of spring coil 22 proximal to distal end 27 comprise stretched coils 28, which extend from distal end 27 to adhesion point 29. A control wire 30 is located within said stretched coils, and the proximal end of control wire 30 is affixed at adhesion point 29. The distal end 27 of stretched coils 28, the distal end of control wire 30, and the distal end of deflection wire 23 are engaged by cap or tip 31.

In FIG. 2 the distal portion 24 of tubing 21 is shown as an integral member of tubing 21. It is within the scope of this invention that distal portion 24 could comprise a separate section of tubing suitably bonded or affixed to tubing 21. Also, the control wire 12 or 30 shown in FIGS. 1 and 2 is optional. If this member is not present, there still may or may not be an adhesion point 11 or 29 located at the proximal end of the stretched coils 10 or 28, respectively.

A preferred embodiment of the invention is shown in FIG. 3. Guidewire 40 comprises tubing 41 having deflection wire 42 arranged axially therein. The distal portion 43 of tubing 41 is tapered, preferably, in successively, concentrically tapered sections wherein the diameter of the tubing 41 is reduced. The distal end 44 of tubing 41 is angularly tapered to a point, which can be seen more clearly in FIGS. 4 and 5. The proximal portion of spring coil 45 is attached to tubing 41 at adhesion point 46. The distal end 47 of spring coil 45 comprises tip 48, which is rounded, preferably semispherical, in shape. Tip 48 is formed by a weld, a braze, solder, or an adhesive such as U.V. curing or cyanoacrylate adhesive.

The coils of spring coil 45 proximal to distal end 47 are stretched as compared to the coils in the remainder of spring coil 45. The stretched coils 49 extend from about 1 to 15 cm, preferably from about 2 to 12 cm, from distal end 47.

Distal end 44 of tubing 41 is attached, preferably welded, brazed, or soldered, to the interior surface of stretched coils 49 at adhesion point 50. Similarly, adhesion point 46 comprises a weld, braze, or solder point encompassing the proximal end of spring coil 45.

In FIGS. 4 and 5 the configuration or shape of the distal end 44 of the tubing can be seen in two different views. The distal portion of tubing 41 has been shaped, preferably ground, to provide a point 51.

According to a preferred embodiment of the invention, the catheter guidewire according to the invention terminates in a control means such as is shown in FIG. 6. Said control means 60 comprises a tip rotation knob 61 and a tip deflection knob 62. The distal portion of tip rotation knob 61 is bonded by suitable bonding means, such as a cyanoacrylate adhesive, to the outer surface of guidewire tubing 63. The proximal portion of tubing 63 terminates within the distal portion of tip rotation knob 61. The distal end of a deflection wire 64 terminates within, and is engaged by a deflection member 65.

The lateral surface of deflection member 65 has threads 66, and the interior surface of the distal end of tip deflection knob 62 has corresponding threads 67. Axial motion of tip deflection knob 62 is restrained by annular projection 68. When tip deflection knob 62 is rotated, deflection member 65 is caused to move in an axial direction, that is, either proximally or distally, a deflection wire 64 moves similarly in axial motion relative to tubing 63. Said movement causes the distal end of the guidewire to deflect either toward or away from its longitudinal axis. Rotation of tip rotation knob 61 causes tubing 63 and deflection wire 64 to rotate together to cause the distal end of the guidewire to rotate.

Preferably the tubing is metal tubing such as stainless steel hypodermic needle tubing having an o.d. of from about 0.010 to 0.040 inch, more preferably from about 0.012 to 0.020 inch, and an i.d. of from about 0.003 to 0.033 inch, more preferably from about 0.005 to 0.017 inch. In the preferred embodiment shown in FIG. 3, the tubing is successively tapered, advantageously by grinding, distally from a point proximal to the distal end of the spring coil. The tubing is ground to dimensions small enough to fit within the spring coil and then, in the distal portion of the tubing, to a "point". For example, the o.d. of the tubing within the spring coil may be from about 0.006 to 0.030 inch, preferably from about 0.008 to 0.020 inch, and the distal end of the tubing may by linearly tapered to a point having a thickness of from about 0.0003 to 0.002 inch, preferably from about 0.0007 to 0.0017 inch. The linear distance from the initial angular taper to the point will be from about 1 to 15 cm, preferably from about 2 to 12 cm.

Spring coil 7, 22, or 45 may be comprised of flat or round metal wire and may comprise one continuous coil or two or more, preferably two, coil sections that are joined together. Preferably the spring coil is comprised of stainless steel round or rectangular wire and has an o.d. of from about 0.008 to 0.035 inch, preferably from about 0.010 to 0.018 inch. Such wire may have, for example, a cross-sectional width of from about 0.0005 to 0.005 inch, preferably from about 0.001 to 0.004 inch, and a cross-sectional length of from about 0.002 to 0.013 inch, preferably from about 0.003 to 0.012 inch. The total length of the guidewire is from about 100 to 190 cm, preferably from about 160 to 180 cm, of which the spring coil comprises from about 25 to 35 cm, more preferably about 30 cm. Moreover, the stretched coils comprise from about 1 to 10 cm, preferably from about 2 to 8 cm, of the spring coil.

The control wire, which is from about 2 to 15 cm in length, preferably comprises small calibre flat tungsten or stainless steel ribbon, having a substantially rectangular cross-section. Suitable wires include a flat stainless steel ribbon having dimensions of from 0.0005 to 0.003 inch×0.002 to 0.004 inch, more preferably about 0.001 inch×0.003 inch.

The deflection wire, which extends the length of the guidewire, preferably comprises a stainless steel wire having an o.d. of from about 0.003 to 0.016 inch, more preferably from about 0.005 to 0.012 inch. The distal portion of the deflection wire is advantageously tapered for flexibility, said tapering preferably starting approximately at the distal portion of the tubing. The tapering can either be constant or stepped to the extent that the distal end of the deflection wire comprises a "point" of either sharp or flattened shape, having a diameter or effective diameter of from about 0.0003 to 0.003 inch, preferably from about 0.0007 to 0.0017 inch.

It is advantageous that the entire length of the guidewire, optionally including the tip, be coated with a lubricous coating. Examples of useful such coatings include polyolefins, a polytetrafluoroethylene, such as is available as TEFLON® from du Pont, as well as hydrogels, polyvinyl chloride, or other suitable plastic or polymeric substances having low friction surfaces.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A steerable guidewire having a deflectable tip which comprises:
    flexible tubing having proximal and distal ends and inner and outer surfaces, said distal end having an external annular recess,
    a helically wound flexible spring coil having proximal and distal ends, the proximal end of said spring coil fitting over said external annular recess and being attached to the flexible tubing at the proximal portion of said external annular recess, and the distal end of said spring coil comprising stretched coils,
    a deflection wire extending through the flexible tubing and spring coil, said deflection wire having proximal and distal ends,
    a rounded tip engaging the distal end of the spring coil and the distal end of the deflection wire, and
    control means attached to the proximal end of the flexible tubing, wherein the proximal end of the deflection wire is engaged by an engaging member, the control means having rotation means and deflection means such that when the rotation means is rotated, the distal end of the spring coil rotates about its longitudinal axis and that when the deflection means is activated, the engaging means moves in an axial direction to cause said deflection wire to move relative to the tubing to cause the distal end of the guidewire to move toward or away from the line of the longitudinal axis of the guidewire.

2. The guidewire of claim 1, wherein the proximal end of the spring coil means is attached to the flexible tubing by a weld, a braze, or solder.

3. The guidewire of claim 1, wherein the spring coil is radiopaque.

4. The guidewire of claim 1, wherein the guidewire has a lubricous coating thereon.

5. The guidewire of claim 1, wherein the guidewire has a control wire having proximal and distal ends, the proximal end of the control wire being attached to said spring coil proximal to the stretched coils and the distal end of the control wire being engaged by the rounded tip.

6. The guidewire of claim 5, wherein the proximal end of the control wire is attached to said spring coil by a weld, a brazed joint, or solder.

7. A steerable guidewire having a deflectable tip which comprises:
    flexible tubing having proximal and distal ends and inner and outer surfaces, the distal end of the flexible tubing having an external annular recess,
    a helically wound flexible spring coil having proximal and distal ends, the proximal end of said spring coil fitting over said external annular recess and being attached by a weld, a brazed joint, or solder to the flexible tubing at the proximal portion of said external annular recess, and the distal end of said spring coil comprising stretched coils,
    a deflection wire extending through the flexible tubing and spring coil, said deflection wire having proximal and distal ends,
    a control wire having proximal and distal ends, the proximal end of the control wire being attached to said spring coil proximal to the stretched coils,
    a rounded tip engaging the distal end of the spring coil, the distal end of the deflection wire, and the distal end of the control wire, and
    control means attached to the proximal end of the flexible tubing, wherein the proximal end of the deflection wire is engaged by an engaging member, the control means having rotation means and deflection means such that when the rotation means is rotated, the distal end of the spring coil rotates about its longitudinal axis and that when the deflection means is activated, the engaging means moves in an axial direction to cause said deflection wire to move relative to the tubing to cause the distal end of the guidewire to move toward or away from the line of the longitudinal axis of the guidewire.

8. The guidewire of claim 7, wherein the proximal end of the control wire is attached to said spring coil by a weld, a brazed joint, or solder.

9. The guidewire of claim 7, wherein the spring coil is radiopaque.

10. The guidewire of claim 7, wherein the guidewire has a lubricous coating thereon.

11. A steerable guidewire having a deflectable tip which comprises:
   flexible tubing having proximal and distal ends and inner and outer surfaces, said distal end having an external annular recess,
   a helically wound flexible spring coil having proximal and distal ends, the proximal end of said spring coil fitting over said external annular recess and being attached to the flexible tubing at the proximal portion of said external annular recess, and the distal end of said spring coil comprising stretched coils,
   a deflection wire extending through the flexible tubing and spring coil, said deflection wire having proximal and distal ends, and
   a rounded tip engaging the distal end of the spring coil and the distal end of the deflection wire.

12. The guidewire of claim 11, wherein the proximal end of the spring coil means is attached to the flexible tubing by a weld, a brazed joint, or solder.

13. The guidewire of claim 11, wherein the spring coil is radiopaque.

14. The guidewire of claim 11, wherein the guidewire has a lubricous coating thereon.

15. The guidewire of claim 11, wherein the guidewire has a control wire having proximal and distal ends, the proximal end of the control wire being attached to said spring coil proximal to the stretched coils and the distal end of the control wire being engaged by the rounded tip.

16. The guidewire of claim 15, wherein the proximal end of the control wire is attached to said spring coil by a weld, a brazed joint, or solder.

17. A steerable guidewire having a deflectable tip which comprises:
   flexible tubing having proximal and distal ends and inner and outer surfaces, the distal end of the flexible tubing having an external annular recess,
   a helically wound flexible spring coil having proximal and distal ends, the proximal end of said spring coil fitting over said external annular recess and being attached by a weld, a brazed joint, or solder to the flexible tubing at the proximal portion of said external annular recess, and the distal end of said spring coil comprising stretched coils,
   a deflection wire extending through the flexible tubing and spring coil, said deflection wire having proximal and distal ends,
   a control wire having proximal and distal ends, the proximal end of the control wire being attached to said spring coil proximal to the stretched coils, and
   a rounded tip engaging the distal end of the spring coil, the distal end of the deflection wire, and the distal end of the control wire.

18. The guidewire of claim 17, wherein the proximal end of the control wire is attached to said spring coil by a weld, a brazed joint, or solder.

19. The guidewire of claim 17, wherein the spring coil is radiopaque.

20. The guidewire of claim 17, wherein the guidewire has a lubricous coating thereon.

* * * * *